United States Patent
Cowton et al.

(10) Patent No.: US 6,299,889 B1
(45) Date of Patent: *Oct. 9, 2001

(54) STABLE ASCORBIC ACID PREPARATION FOR TOPICAL USE

(75) Inventors: Lorraine M. Cowton, Cornwall, NY (US); John A. Duffy, West Milford, NJ (US); Michele C. Duggan, Middletown, NY (US)

(73) Assignee: Avon Products, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,806

(22) Filed: Sep. 10, 1998

(51) Int. Cl.[7] ................................ A61K 6/00; A61K 31/34
(52) U.S. Cl. ......................... 424/401; 514/474; 514/781; 514/844
(58) Field of Search ............................ 424/401; 514/474, 514/781, 844

(56) References Cited

U.S. PATENT DOCUMENTS

| | | | |
|---|---|---|---|
| 2,623,002 | 12/1952 | Fricke | 167/81 |
| 4,036,948 | 7/1977 | Kitamori et al. | 424/32 |
| 4,372,874 | 2/1983 | Modrovich | 436/176 |
| 4,393,076 | 7/1983 | Noda et al. | 424/317 |
| 4,818,521 | 4/1989 | Tamabuchi | 424/62 |
| 4,938,951 | 7/1990 | Leung et al. | 424/59 |
| 4,983,382 | * 1/1991 | Wilmott et al. | 424/62 |
| 5,078,989 | 1/1992 | Ando et al. | 424/62 |
| 5,140,043 | 8/1992 | Darr et al. | 514/474 |
| 5,153,230 | 10/1992 | Jaffery | 514/847 |
| 5,308,621 | 5/1994 | Taylor et al. | 424/401 |
| 5,371,107 | 12/1994 | Hotzel et al. | 514/474 |
| 5,409,693 | 4/1995 | Perricone | 424/59 |
| 5,422,366 | 6/1995 | Mintzis et al. | 514/474 |
| 5,587,149 | 12/1996 | Punto et al. | 424/59 |
| 5,703,041 | 12/1997 | Afriat et al. | 514/2 |
| 5,736,567 | 4/1998 | Cantin et al. | 514/474 |
| 5,750,123 | 5/1998 | Znaiden et al. | 424/407 |
| 5,902,591 | * 5/1999 | Herstein | 424/401 |

FOREIGN PATENT DOCUMENTS

| | | |
|---|---|---|
| WO 98/00102 | 1/1998 | (WO) . |
| WO 98/00103 | 1/1998 | (WO) . |
| WO98/10742 | 3/1998 | (WO) . |
| 98/23152 | * 6/1998 | (WO) . |

OTHER PUBLICATIONS

The Merck Index Tenth Edition item 4763.
The Condensed Chemical Dictionary Eighth Edition pp. 180, 734. 1971.
Hawley's Condensed Chemical Dictionary Eleventh Edition p. 972. 1987.

* cited by examiner

Primary Examiner—Thurman K. Page
Assistant Examiner—Lakshmi Channavajjala
(74) Attorney, Agent, or Firm—Ohlandt, Greeley, Ruggiero & Perle, LLP

(57) ABSTRACT

Stable cosmetic compositions containing high levels of ascorbic acid, relatively low levels of water, varying levels of polyhydric alcohol, and organic carbonate are disclosed. The compositions may also include monohydric alcohol or hydroxyalkyl cellulose or both. The compositions are homogeneous solutions, and can be adapted to be topically applied to the skin to impart appearance benefits thereto.

33 Claims, No Drawings

STABLE ASCORBIC ACID PREPARATION FOR TOPICAL USE

BACKGROUND OF THE INVENTION

1. Field Of The Invention

The present invention relates generally to stable ascorbic acid compositions that are homogeneous solutions suitable for topical use. More specifically, the present invention relates to homogeneous cosmetic preparations incorporating stabilized ascorbic acid that can be topically applied to human skin to impart beneficial appearance effects thereto.

2. Description Of The Prior Art

It is well known that ascorbic acid, synonymously referred to herein as Vitamin C, is essential to the maintenance of a healthy and attractive skin appearance in humans. Vitamin C helps to stimulate and regulate the production of collagen in human skin tissue thus retarding the formation of wrinkles and helping to maintain a healthier and younger looking appearance. Vitamin C also helps to minimize lipid oxidation and cellular damage resulting from prolonged exposure to the sun's ultraviolet rays. By doing so, it counteracts premature aging of the skin. It is generally believed that ascorbic acid inhibits the formation of melanin that can lead to skin discoloration during the aging process, and inhibits the release of histamine from cellular membranes that can lead to allergenic reactions, particularly among individuals with sensitive skin.

Because of these many beneficial effects, it has long been desired to deliver effective concentrations of ascorbic acid percutaneously and directly to the underlying tissue matrix of the skin, i.e. the dermal layer, via a topically applied and cosmetically elegant carrier or base.

Ascorbic acid is appreciably soluble in water. However, it oxidizes rapidly in aqueous solutions. Therefore, it cannot be stabilized in such a medium at the sufficiently high concentrations required to achieve the desired appearance enhancement effect on the skin. On the other hand, solubility of ascorbic acid in non-aqueous media is quite limited so that a large amount of a solvent, such as ethanol, is required to dissolve limited amounts of ascorbic acid. Thus, the limited solubility of ascorbic acid has, heretofore, prevented anhydrous and low water systems from achieving ascorbic acid concentration and efficacy levels required for producing the above described appearance enhancement effect. For this reason, ascorbic acid has been heretofore used in cosmetic formulations only in relatively low concentrations. As a result, prior attempts to develop and to market acceptable cosmetic formulations containing efficacious concentrations of stabilized ascorbic acid have generally met with limited success.

Ascorbic acid is unstable in the presence of oxygen and is rapidly oxidized to dehydroascorbic acid. In body cells, glutathione can reverse the ascorbic acid dehydroascorbic acid conversion so that a pool of ascorbate distributed throughout the body can be maintained.

Aside from preventing scurvy, ascorbic acid is essential to many body or biological functions. The most notable function is the synthesis of collagen, the major fibrillar component of dermal connective tissue, comprising approximately 70 to 80% of the dry weight of the dermis. The essential role of ascorbic acid in the formation and maintenance of collagen as well as in other biological functions and processes has been summarized in U.S. Pat. No. 4,983,382 to Wilmott, et al, which is owned by the assignee of the present invention. The contents of U.S. Pat. No. 4,983,382 are incorporated herein by reference.

U.S. Pat. No. 4,983,382 suggests that replenishing dermal tissues with ascorbic acid percutaneously delivered through the stratum corneum can impart beneficial appearance effects to the skin, including improved tone and luster, a decrease in fine lines and wrinkles, and improved elasticity. However, the compositions disclosed in that patent have ethanol at a concentration of at least forty percent. These compositions do not exhibit sufficient stability to maintain high levels of ascorbic acid concentrations for sufficiently long periods of time. Therefore, they do not generally possess the performance level necessary for the above mentioned skin appearance enhancement effect in cosmetic formulations. To overcome this shortcoming, it is recommended in U.S. Pat. No. 4,983,382, described above, and also in U.S. Pat. No. 5,140,043, to Darr, to store the cosmetic formulation samples in bottles that are impervious to ultraviolet light and to preferably provide with a headspace containing an inert gas.

SUMMARY OF THE INVENTION

It is an object of the present invention to provide a stable ascorbic acid composition that contains high levels of ascorbic acid but does not require high levels of water to produce homogeneous solutions.

It is another object of the present invention to provide a stable ascorbic acid composition that contains high levels of ascorbic acid and lower levels of ethanol than used in the prior art, to produce homogeneous ascorbic acid solutions.

It is a further object of the present invention to provide a process for preparing a homogeneous ascorbic acid composition.

It is still a further object of the present invention to provide a method of improving the appearance of skin using the stable ascorbic acid composition of the present invention.

The composition of the present invention basically comprises: (a) ascorbic acid; (b) a polyhydric alcohol; (c) an organic carbonate; and (d) water. The composition of the present invention may further comprise: (e) a monohydric alcohol and/or (f) a hydroxyalkyl cellulose.

The present invention further includes a process for preparing a homogeneous ascorbic acid composition, comprising: preparing a mixture of the ingredients of the above composition, and thereafter, optionally filtering the prepared composition to remove insoluble particles, if present.

The present invention still further includes a method of improving the appearance of skin using the stable ascorbic acid composition of the present invention. The method comprises topically applying the ascorbic acid composition to an area of skin to be affected such that said ascorbic acid is percutaneously absorbed by said skin and thereafter, optionally applying a moisturizer to said area of skin.

Against the foregoing background, it has been discovered that ascorbic acid can be stabilized indefinitely in a composition adapted to topical application to the skin. In the composition, it is desired to achieve as high an amount of ascorbic acid as possible yet maintain the solubility and stability of the ascorbic acid in the composition. Accordingly, the composition should have as little water as possible in order to achieve the stability desired. In addition, ethanol should be minimized to avoid adversely effecting the ascorbic acid concentration.

DESCRIPTION OF THE PREFERRED EMBODIMENTS

As used herein the terms "solution", "preparation", "composition", and "compositions" are to be used interchangeably. The terms "cosmetic", "cosmetic preparation" and "cosmetic composition" include articles intended to be rubbed, poured, sprinkled, or sprayed on, introduced onto, or otherwise applied to the human or animal body or any part thereof for cleaning, beautifying, promoting attractiveness or altering the appearance. They also include articles intended for use as a component in sun screening compositions, medicinal and first aid creams and the like.

In accordance with the present invention, ascorbic acid is stabilized in a cosmetic composition adapted for topical application onto human skin. As a suitable vehicle for the ascorbic acid, a stable composition is provided having desirable cosmetic qualities, namely, an agreeable, pleasant feel and appearance when topically applied to skin. The organic ingredients are preferably selected to produce a cosmetically elegant formulation that facilitates rapid percutaneous absorption of the stabilized ascorbic acid contained therein when topically applied to the skin, whereupon beneficial effects resulting in enhanced skin appearance may be achieved.

The stable composition or compositions according to the present invention are homogeneous solutions. The homogeneous solution includes ascorbic acid, a polyhydric alcohol, an organic carbonate and water. It can further contain a monohydric alcohol and/or a hydroxyalkyl cellulose.

In the composition of the present invention, ascorbic acid is present at a level preferably in the range from about 0.1 wt % to about 16 wt % and more preferably from 8 wt % to 12 wt % of the total weight of the composition.

Silo Ascorbic acid, L-ascorbic acid and Vitamin C are the equivalent chemical names given to a white odorless crystalline solid having the formula $C_6H_8O_6$ and a molecular weight of 176.13.

TABLE 1 (below) lists the solubility of ascorbic acid in a variety of solvents. TABLE 1 shows that ascorbic acid is relatively soluble in aqueous media but is relatively insoluble in organic solvents, such as alcohols, glycols, fats and oils.

TABLE 1

| Solubility of Ascorbic Acid (g/ml) | |
| --- | --- |
| water | 0.33 |
| 95% ethanol | 0.03 |
| absolute ethanol | 0.02 |
| glycerol USP | 0.01 |
| propylene glycol | 0.03 |

TABLE 1-continued

| Solubility of Ascorbic Acid (g/ml) | |
| --- | --- |
| oils | insoluble |
| fats | insoluble |
| fat solvents | insoluble |

We have now unexpectedly discovered stable ascorbic acid compositions that contain high levels of ascorbic acid and do not require high levels of water and ethanol to produce stable, homogeneous solutions. Furthermore, they do not require nitrogen filled headspace or bottles that are impervious to ultraviolet light, even for long term storage.

Referring to TABLE 1, it is shown that ascorbic acid is even less soluble in ethanol than it is in propylene glycol (about 2 wt %). Therefore, the effect of blending ethanol with propylene glycol would be to reduce the solubility level of ascorbic acid in the organic solvent blend. In the present invention, this effect is balanced not only by the addition of small amounts of water to increase the solubility of ascorbic acid, but also by the addition of the remaining ingredients of the composition, including, particularly, an organic carbonate and, optionally, a hydroxyalkyl cellulose.

Preferably, about 0.1 to about 12 wt % and, more preferably, from 8.0 wt % to 12 wt % water may be added without adversely affecting the stability of the ascorbic acid dissolved in the compositions of the present invention, provided that higher concentrations of ascorbic acid are also used. For example, in accordance with the present invention, up to about 16 wt % ascorbic acid may be dissolved/stabilized at water levels of up to about 12 wt %. However, when lower levels of ascorbic acid are used, similarly low levels of water should preferably be used since the amount of stabilized ascorbic acid varies inversely with the amount of water. Accordingly, it is preferred that the weight ratio of ascorbic acid to water is at least about 1:1.

A significant component of the composition comprises a polyhydric alcohol, optionally in combination with a monohydric alcohol. The polyhydric alcohol and the monohydric alcohol, if present, are preferably polar compounds that are compatible with water and are acceptable for cosmetic use.

Suitable polyhydric alcohols include ethylene glycol, 1,2-propylene glycol, 1,3-propanediol, 1,2-butylene glycol, 2,3-butylene glycol, 1,4-butanediol, 1,2-hexylene glycol, diethylene glycol, dipropylene glycol, polyethylene glycol, polypropylene glycol, glycerin, trimethylolpropane, pentaerythritol, sorbitol, and a mixture thereof. Of these polyhydric alcohols, 1,2-propylene glycol and glycerin are preferred, and a mixture thereof is particularly preferred. The polyhydric alcohol is preferably about 20 wt % to about 85 wt % and more preferably, from 35 wt % to 45 wt % of the total composition.

Ascorbic acid is soluble in propylene glycol at a level of about 4 wt %. However, propylene glycol if used alone is not cosmetically elegant because of its oily feel and viscous consistency. On the other hand, when propylene glycol is used in combination with a monohydric alcohol such as ethanol, the percutaneous absorption of the ascorbic acid and the overall aesthetic feel of the cosmetic are substantially improved. Accordingly, a mixture comprising propylene glycol and ethanol is particularly preferred.

The composition of the present invention includes an organic carbonate for promoting solubility of the ascorbic acid when used in combination with the other ingredients of the present invention. The organic carbonates suitable for use in the present composition include linear and cyclic carbonates. Examples of such linear carbonates include dihydrocarbyl carbonates such as diethyl carbonate, diisopropyl carbonate, dibutyl carbonate and the like. Examples of the cyclic carbonates include five-membered, six-membered and seven-membered cyclic carbonates. Five-membered cyclic carbonates, referred to herein as hydrocarbylene carbonates, are preferred. The preferred hydrocarbylene carbonate is selected from the group consisting of ethylene carbonate, propylene carbonate (1,2-propylene carbonate), 1,2-butylene carbonate, 2,3-butylene carbonate, and mixtures thereof. The most preferred hydrocarbylene carbonate is propylene carbonate.

Because propylene carbonate is non-toxic, it can be used at relatively high concentrations in the present compositions without affecting the cosmetic utility of the present invention. The amount of the organic carbonate is preferably in the range from about 0.3 wt % to about 25 wt % and more preferably from 1.0 wt % to 10 wt % of the composition.

Suitable monohydric alcohols, if present, include methanol, ethanol, 1-propanol, 2-propanol, 2-methyl-1-propanol, 1-butanol, 2-butanol, 2-methyl-2-propanol, 2-propene-1-ol, 2-propyn-1-ol, 2-methoxy-1-ethanol, 1-methoxy-2-propanol, 2-methoxy-1-propanol and mixtures thereof. Of these monohydric alcohols, ethanol is preferred.

The monohydric alcohol may be present at a level up to 38 wt % of the total weight of the composition. However, it is preferably from about 5 to about 38 wt % and more preferably from 25 to 35 wt % of the total weight of the composition. Clearly, the prior art discussed above requires ethanol in levels of 40% or greater.

Hydroxyalkyl cellulose is a known thickening agent and is used for that purpose in the present composition. However, it has been unexpectedly discovered that, in addition to thickening, hydroxyalkyl cellulose increases the solubility of ascorbic acid when used in combination with the other ingredients of the present composition.

The preferred hydroxyalkyl cellulose includes the lower hydroxyalkyl derivatives, such as hydroxyethyl cellulose, hydroxypropyl cellulose and mixtures thereof. The most preferred hydroxyalkyl cellulose is hydroxypropyl cellulose.

The amount of hydroxyalkyl cellulose is preferably in the range from about 0.01 wt % to about 3 wt % and more preferably from 0.1 wt % to 1.0 wt % of the composition. Because of the relatively low solubility of the hydroxyalkyl cellulose in the solvent systems used in the present invention, the hydroxyalkyl cellulose, if present at levels greater than 3 wt %, may result in non-homogeneous systems. In these cases, the undissolved hydroxyalkyl cellulose can be removed by filtration to produce homogeneous solutions that are within the scope of the present invention.

In a preferred embodiment, both a hydroxyalkyl cellulose and an organic carbonate are present in the present composition and produce the observed solubility promoting effect. The preferred organic carbonate to hydroxyalkyl cellulose ratio is from about 5:1 to about 50:1, and the most preferred organic carbonate to hydroxyalkyl cellulose ratio is from about 10:1 to about 30:1.

Thus, the preferred homogeneous and stable ascorbic acid containing compositions or solutions of the present invention have about 0.1 to about 16 wt % ascorbic acid, about 20 to about 85 wt % polyhydric alcohol, about 0.3 to about 25 wt % organic carbonate, about 0.1 to about 12 wt % water, and, optionally, about 5 to about 38 wt % monohydric alcohol, and about 0.01 to about 3 wt % hydroxyalkyl cellulose. More preferably, the homogeneous and stable ascorbic acid compositions of the present invention have about 8.0 wt % to about 10 wt % ascorbic acid, about 25 wt % to about 35 wt % monohydric alcohol, about 35 wt % to about 45 wt % polyhydric alcohol, about 0.1 wt % to about 1.0 wt % hydroxyalkyl cellulose, about 1.0 wt % to about 10 wt % organic carbonate, and about 8.0 wt % to about 12 wt % water.

The composition of the present invention is prepared by blending ascorbic acid, a polyhydric alcohol, an organic carbonate and water, and thereafter, optionally filtering the so prepared composition to remove insoluble particles, if present.

The ingredients are mixed together at room temperature in a suitable, standard mixing vessel. Optionally, a monohydric alcohol, and/or a hydroxyalkyl cellulose and various other cosmetic ingredients may be added during blending. Such ingredients include emollients, moisturizers, colorants, fragrance, preservatives, and antioxidants. Lastly, ascorbic acid, preferably in powder form, is added to the mixing vessel. The final composition may then be packaged in ordinary containers for distribution to consumers. Ascorbic acid, either in fine granular form or in ultrafine powder form, is commercially available from Roche Vitamins Inc., Hoffman-La Roche, Nutley, N.J.

In practice, the compositions of the present invention may be applied topically, preferably after cleansing the skin area to be affected with mild soap and warm water. After application, a standard moisturizing lotion or cream is optionally applied to the same skin area without affecting the efficacy of the ascorbic acid composition.

The present invention discloses stable compositions having ascorbic acid, which compositions are cosmetically elegant. When these compositions are topically applied to human skin, they produce skin appearance benefits including, but not limited to, improvements in luster, tone, elasticity, clarity, and a reduction in sagging, sallowness, photo damage and fine lines, wrinkles, and size of pores. The compositions of the present invention provide a stable environment for formulating ascorbic acid for a long shelf life. By doing so, these compositions also avoid the extraordinary packaging requirements of the prior art and permit relatively high levels of ascorbic acid to be topically applied to the skin to impart skin appearance benefits thereto.

The following examples illustrate the various embodiments of the present invention and the superior performance of the compositions prepared in accordance with its teachings.

EXAMPLE 1

PART 1:

Five composition samples, Composition A, Composition B, Composition C, Composition D and Composition E, shown in TABLE 2, were prepared by mixing the ingredients at room temperature. Compositions A, B, C and D are compositions made in accordance with the present invention. Composition E is a composition made in accordance with U.S. Pat. No. 4,983,382 discussed above. The total calculated water content of each composition, which is the sum of the water present in the ethanol and the added demineralized water, was as follows: Composition A, 9.98 wt %; Composition B, 10.00 wt %; Composition C, 9.98 wt %; Composition D, 9.99 wt %; and Composition E, 14.59 wt %. The high level of ethanol required for the preparation of compositions in accordance with U.S. Pat. No. 4,983,382 and the absence of the solubility promoting ingredients such as the organic carbonates of the present invention precluded the preparation of compositions having high levels of ascorbic acid.

PART 2:

Two sets of samples with each set having three samples per set were prepared for testing the stability of ascorbic acid compositions of the present invention.

In the first set, the first sample was prepared by adding a measured amount of Composition A containing 10 wt % ascorbic acid to one ounce clear glass Boston round bottle and sealing the bottle after leaving a 5% by volume headspace above the materials in the sample. The second and third samples were similarly prepared by varying the amount of material added to leave a 25% headspace and 50% headspace, respectively, in the second and the third samples. The headspace contained ambient air.

The three samples (first set) were kept at a temperature of 40 degrees F and the ascorbic acid level was quantified at regular intervals over a period of twelve (12) weeks by titration as described below.

In the second set, the procedure described for the first set was repeated but the resulting samples were exposed to heat at 110 degrees F. As before, the ascorbic acid level was quantified at regular intervals over a period of twelve (12) weeks.

The amount of ascorbic acid present in a sample was determined as follows:

The sample was dispersed in chloroform and the ascorbic acid was extracted from the chloroform using a 0.4 N sulfuric acid solution. The ascorbic acid was then titrated with 0.1 N iodine to a blue-black endpoint using a starch indicator. In the case of multiple runs, the numbers were averaged. The results thus obtained are summarized in TABLE 3.

TABLE 2

ASCORBIC ACID COMPOSITIONS
(Amounts in Weight %)

| COMPOSITION | A | B | C | D | E |
|---|---|---|---|---|---|
| ALCOHOL SD 40B[a] | 33.80 | — | 33.85 | 34.00 | 61.30 |
| DEMINERALIZED WATER | 7.45 | 10.00 | 7.45 | 7.45 | 10.00 |
| HYDROXYPROPYL CELLULOSE | 0.50 | 0.50 | 0.50 | 0.50 | 0.50 |
| PROPYLENE GLYCOL | 21.00 | 21.00 | 21.00 | 21.00 | 21.00 |
| GLYCERIN | 21.00 | 21.00 | 21.00 | 21.00 | — |
| BUTYLATED HYDROXYTOLUENE | 0.20 | 0.20 | 0.15 | — | 0.20 |
| PROPYLENE CARBONATE | 6.00 | 6.00 | 6.00 | 6.00 | — |
| ASCORBIC ACID (ULTRAFINE POWDER) | 10.00 | 10.00 | 10.00 | 10.00 | — |
| FRAGRANCE | 0.05 | 0.01 | 0.05 | 0.05 | — |
| ALCOHOL SD 40B (ANHYDROUS)[b] | — | 31.29 | — | — | — |
| PROPYLENE GLYCOL DIPELARGONATE | — | — | — | — | 1.00 |
| OCTYL PELARGONATE | — | — | — | — | 1.00 |
| ASCORBIC ACID (FINE GRANULAR) | — | — | — | — | 5.00 |

[a]ALCOHOL SD 40B is 92.52 wt % ethanol and 7.48 wt % water
[b]ALCOHOL SD 40B (ANHYDROUS) is 100 wt % ethanol

TABLE 3

ASCORBIC ACID HEADSPACE STUDY
COMPOSITION A

| Weeks | % Headspace | % Ascorbic Acid (40° F.) | % Degradation (40° F.) | % Ascorbic Acid (110° F.) | % Degradation (110° F.) |
|---|---|---|---|---|---|
| 0 | 5 | 10.12 | — | 10.12 | — |
| 2 | 5 | 10.18 | 0.00 | 10.07 | 0.50 |
| 4 | 5 | 10.11 | 0.10 | 9.96 | 1.60 |
| 8 | 5 | 10.01 | 1.00 | 9.80 | 3.20 |
| 12 | 5 | 10.15 | 0.00 | 9.84 | 2.80 |
| 0 | 25 | 10.12 | — | 10.12 | — |
| 2 | 25 | 10.08 | 0.40 | 10.03 | 0.90 |
| 4 | 25 | 10.05 | 0.70 | 9.91 | 2.00 |
| 8 | 25 | 9.97 | 1.50 | 9.75 | 3.70 |
| 12 | 25 | 10.04 | 0.80 | 9.72 | 4.00 |
| 0 | 50 | 10.12 | — | 10.12 | — |
| 2 | 50 | 10.10 | 1.00 | 9.91 | 2.10 |
| 4 | 50 | 10.00 | 1.20 | 9.75 | 3.70 |
| 8 | 50 | 9.90 | 2.20 | 9.54 | 5.70 |
| 12 | 50 | 9.90 | 2.20 | 9.48 | 6.30 |

Referring to TABLE 3, it can be clearly seen that, within an experimental error of about three percent, the ascorbic acid-containing compositions of the present invention did not suffer significant losses of ascorbic acid during the extended periods of exposure to heat and oxygen. Thus, TABLE 3 shows that the ascorbic acid-containing Composition A of the present invention has excellent ascorbic acid stability over long periods of time.

EXAMPLE 2

Compositions A through D, each having 10% ascorbic acid were prepared in accordance with the present invention. Composition E was prepared in accordance with U.S. Pat.

No. 4,983,382. All five compositions were prepared by the procedure described in EXAMPLE 1, PART 1, above to produce samples. Each sample had approximately 5% headspace. The samples were then exposed to the following temperatures: 40 degrees F, 100 degrees F and 110 degrees F. As before, the ascorbic acid level was quantified at regular intervals over a period of twelve (12) weeks by titration as described in EXAMPLE 1, PART 2, above. The results are summarized in TABLE 4.

TABLE 4

ASCORBIC ACID STABILITY STUDY

| Composition | | A | | B | | C | | D | | E | |
|---|---|---|---|---|---|---|---|---|---|---|---|
| Weeks | T(° F.) | % AA | % Dgrd | % AA | % Dgrd | % AA | % Dgrd | % AA | % Dgrd | % AA | % Dgrd |
| 0 | Ambient | 10.26 | — | 10.33 | — | 10.06 | — | 10.11 | — | 5.25 | — |
| 4 | 40 | 10.26 | 0.00 | 10.13 | 1.90 | 10.18 | 0.00 | 10.21 | 0.00 | 5.14 | 2.10 |
| 4 | 100 | 10.02 | 0.60 | — | — | 10.16 | 0.00 | 10.15 | 0.00 | — | — |
| 4 | 110 | — | — | 10.13 | 1.90 | 10.12 | 0.00 | 10.12 | 0.00 | 5.09 | 3.00 |
| 8 | 40 | 10.26 | 0.00 | 10.21 | 1.10 | 10.20 | 0.00 | 10.22 | 0.00 | 5.07 | 3.40 |
| 8 | 100 | 10.15 | 1.00 | — | — | 10.06 | 0.00 | 10.10 | 0.10 | — | — |
| 8 | 110 | — | — | 10.08 | 2.40 | 10.02 | 0.30 | 10.04 | 0.70 | 4.98 | 5.10 |
| 12 | 40 | 10.32 | 0.00 | 10.23 | 1.00 | 10.22 | 0.00 | 10.24 | 0.00 | 5.07 | 3.40 |
| 12 | 100 | 10.16 | 1.00 | 10.07 | 2.50 | 10.09 | 0.00 | 10.15 | 0.00 | 4.98 | 5.10 |
| 12 | 110 | 10.09 | 1.70 | 9.99 | 3.30 | 10.03 | 0.00 | 9.99 | 1.20 | 4.99 | 5.00 |

T(° F.) = Temperature in Degrees Fahrenheit
% AA = Percent Ascorbic Acid
% Dgrd = Percent Degradation Referring to TABLE 4, it is clearly shown that, within an experimental error of about three percent, the ascorbic acid-containing compositions of the present invention did not suffer significant losses of ascorbic acid during the extended periods of exposure to heat and oxygen. For example, it is clearly shown in TABLE 4, that after twelve weeks, the percent degradation of ascorbic acid in Compositions A and B was 1.7 and 3.3, respectively, whereas the percent degradation in Composition E during that same period was 5.0. It is further shown in that, over a period of eight weeks, Compositions C and D of the present invention had 0.3 and 0.7 percent degradation, respectively, whereas the percent degradation in Composition E was 5.10 percent during the same period. Based on the above results, it is concluded that the ascorbic acid-containing Compositions A, B, C and D of the present invention have superior ascorbic acid stability than Composition E prepared in accordance with U.S. Pat. No. 4,983,382.

EXAMPLE 3

Composition F, a homogeneous solution in accordance with the present invention containing 15 wt % ascorbic acid was prepared by mixing the ingredients shown in TABLE 5 at room temperature. The total calculated water content of Composition F, which is the sum of the water present in the ethanol and the added demineralized water, was 8.73 wt %.

TABLE 5

ASCORBIC ACID COMPOSITION
(Amounts in Weight %)

| COMPOSITION | F |
|---|---|
| ALCOHOL SD 40B[a] | 17.05 |
| DEMINERALIZED WATER | 7.45 |

TABLE 5-continued

ASCORBIC ACID COMPOSITION
(Amounts in Weight %)

| COMPOSITION | F |
|---|---|
| HYDROXYPROPYL CELLULOSE | 0.50 |
| PROPYLENE GLYCOL | 21.00 |
| GLYCERIN | 21.00 |
| PROPYLENE CARBONATE | 18.00 |
| ASCORBIC ACID (ULTRAFINE POWDER) | 15.00 |

[a]ALCOHOL SD 40B is 92.52 wt % ethanol and 7.48 wt % water.

It is to be understood that the examples shown and described above are not intended to limit the scope of the present invention but to illustrate various embodiments thereof. Therefore, it would be apparent to those skilled in the art to make variations and modifications thereof without departing from the scope of the appended claims.

Wherefore we claim:

1. A solution, comprising:
   ascorbic acid;
   polyhydric alcohol;
   about 0.3 wt % to about 25 wt % organic carbonate; and
   water,
   wherein the polyhydric alcohol, organic carbonate and water are present in amounts effective to stabilize the ascorbic acid.

2. The solution of claim 1, wherein the ascorbic acid is about 0.1 wt % to about 16 wt % of the total weight of the solution.

3. The solution of claim 1, wherein the ascorbic acid is from 8.0 wt % to 12 wt % of the total weight of the solution.

4. The solution of claim 1, wherein the polyhydric alcohol is selected from the group consisting of ethylene glycol, 1,2-propylene glycol, 1,3-propanediol, 1,2-butylene glycol, 2,3-butylene glycol, 1,4-butanediol, 1,2-hexylene glycol, diethylene glycol, dipropylene glycol, polyethylene glycol, polypropylene glycol, glycerin, trimethylolpropane, pentaerythritol, sorbitol, and a mixture thereof.

5. The solution of claim 1, wherein the polyhydric alcohol is about 20 wt % to about 85 wt % of the total weight of the solution.

6. The solution of claim 5, wherein the polyhydric alcohol is from 35 wt % to 45 wt % of the total weight of the solution.

7. The solution of claim 1, wherein the organic carbonate is hydrocarbylene carbonate.

8. The solution of claim 7, wherein the hydrocarbylene carbonate is selected from the group consisting of ethylene carbonate, propylene carbonate, 1,2-butylene carbonate, 2,3-butylene carbonate, and mixtures thereof.

9. The solution of claim 1, wherein the organic carbonate is from 1.0 wt % to 10 wt % of the total weight of the solution.

10. The solution of claim 1, wherein the water is from 8.0 wt % to 12 wt % of the total weight of the solution.

11. The solution of claim 1, further comprising monohydric alcohol.

12. The solution of claim 11, wherein the monohydric alcohol is selected from the group consisting of methanol, ethanol, 1-propanol, 2-propanol, 2-methyl-1-propanol, 1-butanol, 2-butanol, 2-methyl-2-propanol, 2-propene-1-ol, 2-propyn-1-ol, 2-methoxy-1-ethanol, 1-methoxy-2-propanol, 2-methoxy-1-propanol and a mixture thereof.

13. The solution of claim 1, wherein the monohydric alcohol is about 5 wt % to about 38 wt % of the total weight of the solution.

14. The solution of claim 1, further comprising hydroxyalkyl cellulose.

15. The solution of claim 14, wherein the hydroxyalkyl cellulose is selected from the group consisting of hydroxyethyl cellulose, hydroxypropyl cellulose and a mixture thereof.

16. The solution of claim 14, wherein the hydroxyalkyl cellulose is about 0.01 wt % to about 3 wt % of the total weight of the solution.

17. The solution of claim 1, further comprising:
monohydric alcohol and
hydroxyalkyl cellulose.

18. The solution of claim 17, wherein the monohydric alcohol is selected from the group consisting of methanol, ethanol, 1-propanol, 2-propanol, 2-methyl-1-propanol, 1-butanol, 2-butanol, 2-methyl-2-propanol, 2-propene-1-ol, 2-propyn-1-ol, 2-methoxy-1-ethanol, 1-methoxy-2-propanol, 2-methoxy-1-propanol and a mixture thereof.

19. The solution of claim 17, wherein the polyhydric alcohol is selected from the group consisting of ethylene glycol, 1,2-propylene glycol, 1,3-propanediol, 1,2-butylene glycol, 2,3-butylene glycol, 1,4-butanediol, 1,2-hexylene glycol, diethylene glycol, dipropylene glycol, polyethylene glycol, polypropylene glycol, glycerin, trimethylolpropane, pentaerythritol, sorbitol, and a mixture thereof.

20. The solution of claim 19, wherein the organic carbonate is hydrocarbylene carbonate.

21. The solution of claim 17, wherein the hydroxyalkyl cellulose is selected from the group consisting of hydroxyethyl cellulose, hydroxypropyl cellulose and a mixture thereof.

22. The solution of claim 17, wherein the ascorbic acid is about 0.1 wt % to about 16 wt % of the total weight of the solution.

23. The solution of claim 22, wherein the polyhydric alcohol is about 20 wt % to about 85 wt % of the total weight of the solution.

24. The solution of claim 17, wherein the monohydric alcohol is about 5 wt % to about 38 wt % of the total weight of the solution.

25. The solution of claim 17, wherein the hydroxyalkyl cellulose is about 0.01 wt % to about 3 wt % of the total weight of the solution.

26. A stable ascorbic acid cosmetic solution, comprising:
ascorbic acid;
about 20 wt % to about 85 wt % polyhydric alcohol;
about 0.3 wt % to about 25 wt % organic carbonate; and
about 0.1 wt % to about 12 wt % water.

27. A process for preparing a homogeneous and stable ascorbic acid cosmetic solution, comprising:
(a) preparing a mixture, comprising:
ascorbic acid;
polyhydric alcohol;
about 0.3 wt % to about 25 wt % organic carbonate; and
water,
wherein the polyhydric alcohol, organic carbonate, and water are present in amounts effective to stabilize the ascorbic acid; and optionally
(b) filtering the prepared mixture to remove insoluble particles, if present.

28. The process of claim 27, wherein the mixture further comprises:
monohydric alcohol; and
hydroxyalkyl cellulose.

29. A method of improving the appearance of skin, comprising:
(a) topically applying to an area of said skin an effective amount of a stable solution comprising:
ascorbic acid;
polyhydric alcohol;
about 0.3 wt % to about 25 wt % organic carbonate; and
water,
wherein said polyhydric alcohol, organic carbonate and water are present in amounts effective to stabilize the ascorbic acid, and thereafter, optionally
(b) applying a moisturizer to said area of skin.

30. The method of claim 29, wherein the stable solution further comprises:
monohydric alcohol; and
hydroxyalkyl cellulose.

31. The solution of claim 1, wherein the water comprises from about 0.1 wt. % to about 12 wt. % of the total weight of the solution.

32. The solution of claim 1, wherein the weight ratio of ascorbic acid to water is at least about 1:1.

33. The solution of claim 26, wherein the ascorbic acid is present from about 0.1 wt % to about 16 wt % of the total weight of the solution.

* * * * *